United States Patent
Oishi

(10) Patent No.: US 9,330,462 B2
(45) Date of Patent: May 3, 2016

(54) OBJECT INFORMATION ACQUIRING APPARATUS AND CONTROL METHOD OF OBJECT INFORMATION ACQUIRING APPARATUS

(71) Applicant: CANON KABUSHIKI KAISHA, Tokyo (JP)

(72) Inventor: Takuji Oishi, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 67 days.

(21) Appl. No.: 14/250,571

(22) Filed: Apr. 11, 2014

(65) Prior Publication Data

US 2014/0321760 A1    Oct. 30, 2014

(30) Foreign Application Priority Data

Apr. 30, 2013 (JP) ................. 2013-095196

(51) Int. Cl.
*G06K 9/68* (2006.01)
*G06T 7/00* (2006.01)
(Continued)

(52) U.S. Cl.
CPC .............. *G06T 7/0014* (2013.01); *A61B 5/0091* (2013.01); *A61B 5/0095* (2013.01);
(Continued)

(58) Field of Classification Search
CPC ............... A61B 8/0816; A61B 5/1455; A61B 5/02225; A61B 5/0095; A61B 5/14551; A61B 5/412; A61B 5/02007; A61B 5/024; A61B 5/748; A61B 2562/0204; A61B 8/5269; G01S 15/8965; G01S 15/8909; G01N 21/1702; G01N 29/2418; G01N 29/2425; G06T 2207/10132; G06T 7/0014; G06T 7/0083; G03B 21/00; H04N 9/3129; G02B 27/50; G02B 6/06; H01S 3/101
USPC .......... 600/316, 407, 443, 447; 382/128, 131, 382/218, 228, 129, 130, 132
See application file for complete search history.

(56) References Cited

U.S. PATENT DOCUMENTS 5,524,623 A * 6/1996 Liu ...................... G01S 7/52077
128/901
2004/0050165 A1* 3/2004 He .......................... G01B 17/02
73/597

(Continued)

FOREIGN PATENT DOCUMENTS

| JP | 2008-188266 | 8/2008 |
|---|---|---|
| JP | 2009-082450 | 4/2009 |
| WO | 2012/086842 | 6/2012 |

OTHER PUBLICATIONS

Office Action issued on Oct. 8, 2015 in counterpart Chinese (P.R. China) patent application 201410169251.2, with translation.
(Continued)

*Primary Examiner* — Vu Le
*Assistant Examiner* — Aklilu Woldemariam
(74) *Attorney, Agent, or Firm* — Fitzpatrick, Cella, Harper & Scinto

(57) ABSTRACT

An object information acquiring apparatus that acquires information inside an object by receiving an acoustic wave that has arrived from inside the object through a layer having an acoustic impedance that is different from that of the object, and analyzing the acoustic wave, the object information acquiring apparatus comprises an acoustic wave probe that receives an acoustic wave and converts the acoustic wave into an electric signal; a whole image generation unit that generates a whole image, which is an image indicating information inside the object, based on the electric signal after the conversion; a partial image generation unit that extracts a partial image, which is a part of the whole image, from the whole image; and a similar image search unit that searches an area similar to the partial image, from the whole image.

16 Claims, 25 Drawing Sheets

(51) Int. Cl.
  *A61B 5/00* (2006.01)
  *G06T 5/00* (2006.01)
  *A61B 8/08* (2006.01)

(52) U.S. Cl.
  CPC .............. *A61B5/7203* (2013.01); *A61B 5/7246* (2013.01); *G06K 9/68* (2013.01); *G06T 5/005* (2013.01); *A61B 5/7264* (2013.01); *A61B 8/5269* (2013.01); *G06T 2207/10132* (2013.01); *G06T 2207/30068* (2013.01)

(56) References Cited

U.S. PATENT DOCUMENTS

| | | | | |
|---|---|---|---|---|
| 2006/0241572 A1* | 10/2006 | Zhou | ............... | A61B 8/12 606/7 |
| 2008/0077011 A1* | 3/2008 | Azuma | ............... | G06T 7/2006 600/443 |
| 2010/0058870 A1* | 3/2010 | Kobayashi | ........ | G01N 21/1702 73/596 |
| 2011/0083511 A1 | 4/2011 | Taki et al. | ............... | 73/602 |
| 2012/0143058 A1 | 6/2012 | Powers et al. | ............... | 600/443 |
| 2012/0223709 A1* | 9/2012 | Schillak | ............ | G01R 33/3621 324/309 |
| 2013/0039147 A1* | 2/2013 | Witte | ................ | A61B 5/0093 367/7 |
| 2013/0072798 A1* | 3/2013 | Tateyama | ................ | A61B 8/14 600/444 |
| 2013/0121106 A1* | 5/2013 | Nishihara | ............ | A61B 5/0073 367/7 |
| 2013/0144150 A1* | 6/2013 | Kim | ................... | A61B 5/0095 600/407 |
| 2013/0160558 A1 | 6/2013 | Oishi | ............... | 73/655 |
| 2013/0261427 A1* | 10/2013 | Oishi | ................... | A61B 5/0095 600/407 |
| 2013/0267856 A1* | 10/2013 | Watanabe | ............ | A61B 5/748 600/476 |
| 2013/0336088 A1* | 12/2013 | Umezawa | ............ | G01S 15/89 367/8 |
| 2014/0018645 A1 | 1/2014 | Wada et al. | ............... | 600/316 |
| 2014/0058245 A1 | 2/2014 | Oishi et al. | ............... | 600/407 |

OTHER PUBLICATIONS

EESR issued on Jul. 22, 2014 in counterpart EPA 14163972.4 (in English).

* cited by examiner

OBJECT INFORMATION ACQUIRING APPARATUS AND CONTROL METHOD OF OBJECT INFORMATION ACQUIRING APPARATUS

BACKGROUND OF THE INVENTION

1. Field of the Invention

The present invention relates to an object information acquiring apparatus and a control method thereof, and more particularly to a technique to remove an artifact caused by the multiple reflection of an acoustic wave.

2. Description of the Related Art

In medical fields, a technique called "photoacoustic tomography" (PAT) has been proposed in recent years as a technique that can image inside an organism non-invasively, and development thereof is progressing. Photoacoustic tomography is a technique to image an internal tissue that generates an acoustic wave by irradiating pulsed light generated from a light source onto an object, and utilizing a photoacoustic effect where an acoustic wave (typically an ultrasound wave) is generated by absorption of the light which propagated and diffused inside the object. By receiving the acoustic wave generated inside the object using an acoustic wave probe and mathematically analyzing and reconstructing the acquired signals, information related to the optical characteristic values inside the object can be visualized. This apparatus is called a "photoacoustic measurement apparatus" or the like.

In an apparatus that acquires information inside an object using an acoustic wave, as with the photoacoustic measurement apparatus, acoustic impedance matching between the object and the acoustic wave probe on the acoustic wave propagation path is required. If there is an area where the acoustic impedance does not match between the object and the acoustic wave probe, the acoustic wave is reflected by this area, and an image cannot be reconstructed normally.

Actually however a reflection layer often exists between the acoustic wave probe and the object, and it is difficult to perfectly match the acoustic impedance on an acoustic wave propagation path. The reflection layer is, for example, a holding plate used for securing an object. Such a holding plate has an acoustic impedance that is different from that of the organism, hence the acoustic wave is reflected by the interface therebetween. The reflected acoustic wave is also reflected by the interface on the opposite side, and attenuates while repeating the reflection between the probe and the object. In other words, the acoustic wave repeatedly enters the probe and appears as an incorrect image in the acoustic wave transmission direction. This false image is called an "artifact". An artifact appears with a stronger intensity as the reflection becomes closer to the specular reflection. This problem occurs not only to photoacoustic measurement apparatuses but also to apparatuses which acquire information inside an object by an acoustic wave, such as an ultrasound measurement apparatus using an ultrasound wave echo.

Techniques to remove an artifact generated by the multiple reflection of an acoustic wave includes the following. For example, Japanese Patent Application Laid-open No. 2009-82450 discloses an imaging apparatus that extracts a signal reflected by an interface of a holding plate, and deletes this signal from the acquired image so as to remove the reflection signal.

SUMMARY OF THE INVENTION

An imaging apparatus according to Japanese Patent Application Laid-open No. 2009-82450 is an apparatus that images information inside an object by transmitting an ultrasound wave into the object and receiving an ultrasound echo reflected from inside the object. In this imaging apparatus, a signal of which form matches with the transmitted acoustic wave signal is regarded as a multiple reflection signal, and is removed.

However a disadvantage of this imaging apparatus is that only an artifact caused by a known signal can be removed.

In a photoacoustic measurement apparatus, an acoustic wave generated inside an object causes multiple reflection between the object and an acoustic probe. The acoustic wave generated inside the object indicates information inside the object, therefore the type of signal that is generated cannot be predicted. Particularly in a photoacoustic measurement apparatus, which is often used for acquiring signals generated by the blood flow on the surface of an organism, an artifact presents a complex shape, reflecting a vascular image of a testee.

The imaging apparatus according to Japanese Patent Application Laid-open No. 2009-82450, on the other hand, is based on the assumption that the form of the multiple reflection signal is always the same, therefore only an artifact caused by an acoustic wave signal transmitted to an object can be removed. In other words, an artifact cannot be removed even if the technique of the imaging apparatus is applied to a photoacoustic measurement apparatus.

With the foregoing in view, it is an object of the present invention to provide an object information acquiring apparatus that can accurately detect an artifact generated by the multiple reflection of an acoustic wave.

The present invention in its one aspect provides an object information acquiring apparatus that acquires information inside an object by receiving an acoustic wave that has arrived from inside the object through a layer having an acoustic impedance that is different from that of the object, and analyzing the acoustic wave, the object information acquiring apparatus comprises an acoustic wave probe that receives an acoustic wave and converts the acoustic wave into an electric signal; a whole image generation unit that generates a whole image, which is an image indicating information inside the object, based on the electric signal after the conversion; a partial image generation unit that extracts a partial image, which is a part of the whole image, from the whole image; and a similar image search unit that searches an area similar to the partial image, from the whole image.

The present invention in its another aspect provides a control method of an object information acquiring apparatus that has an acoustic probe to receive an acoustic wave, and acquires information inside an object by receiving an acoustic wave that has arrived from inside the object through a layer having an acoustic impedance that is different from that of the object and analyzing the acoustic wave, the control method comprises a reception step of receiving an acoustic wave and converting the acoustic wave into an electric signal using the acoustic wave probe; a whole image generation step of generating a whole image, which is an image indicating information inside the object, based on the electric signal after the conversion; a partial image generation step of extracting a partial image, which is a part of the whole image, from the whole image; and a similar image search step of searching an area similar to the partial image, from the whole image.

According to the present invention, an object information acquiring apparatus that can accurately detect an artifact generated by the multiple reflection of an acoustic wave can be provided.

Further features of the present invention will become apparent from the following description of exemplary embodiments with reference to the attached drawings.

DESCRIPTION OF THE EMBODIMENTS

Embodiment 1

Embodiment 1 of the present invention will now be described with reference to the drawings.

A photoacoustic measurement apparatus according to Embodiment 1 is an apparatus that images information inside an organism (object) by irradiating measurement light onto the object, and receiving and analyzing an acoustic wave which is generated inside the object by the measurement light. The photoacoustic measurement apparatus also has a function to detect an artifact generated by the multiple reflection of the acoustic wave between a probe and the object, and notify the result to the operator.

<Overview of Artifact Detection>

An overview of a principle of the appearance of an artifact and a detection method thereof will be described first with reference to FIG. 1.

Figure 1A:
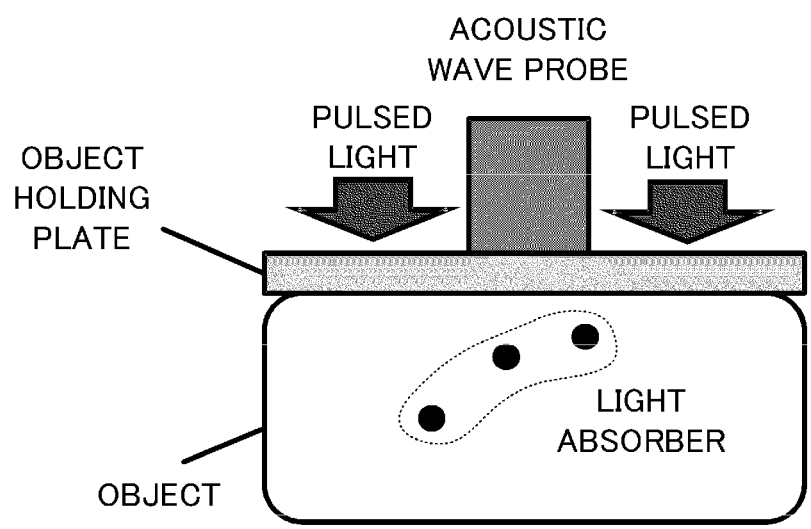
FIG. 1A to FIG. 1D are diagrams depicting a principle of the appearance of an artifact in a measurement image.

As illustrated in FIG. 1A, the photoacoustic measurement apparatus according to this embodiment compresses and holds an object by an object holding plate, and performs the photoacoustic measurement by irradiating pulsed light in this state.

When the pulsed light is irradiated onto the object through the object holding plate, a part of the energy of the light propagated inside the object is absorbed by a light absorber (e.g. blood), and an acoustic wave is generated by the thermal expansion of the light absorber. The acoustic wave generated inside the object is received by an acoustic wave probe through the object holding plate, and is analyzed and imaged by a processing unit. As a result, an image shown in FIG. 1B, for example (image to indicate the entire measurement area, hereafter called a "whole image"), is acquired.

Figure 1B:
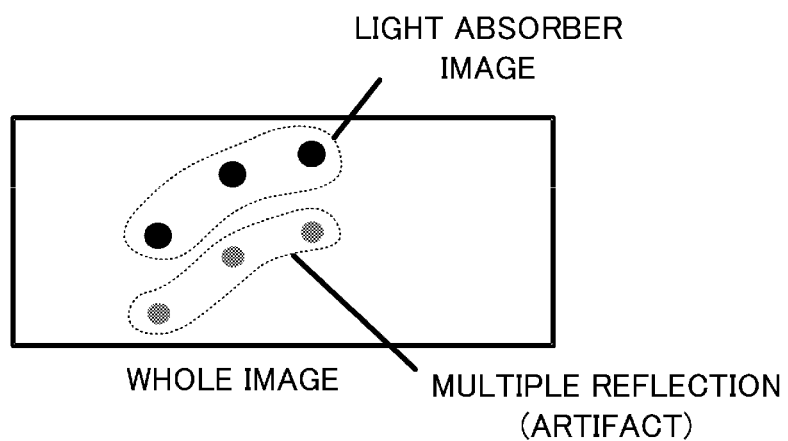

The light absorber image shown in FIG. 1B is an image that should be acquired by measurement. However the acoustic wave generated from the light absorber, passing through the object holding plate, is reflected by the interface thereof, and the reflected acoustic wave repeatedly enters the acoustic wave probe. As a result, the entered acoustic waves are imaged and appear in the whole image as an artifact (false image).

Figure 1C:
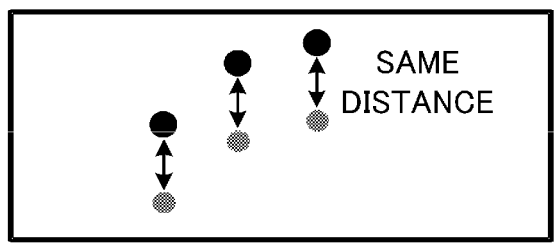
Figure 1D:
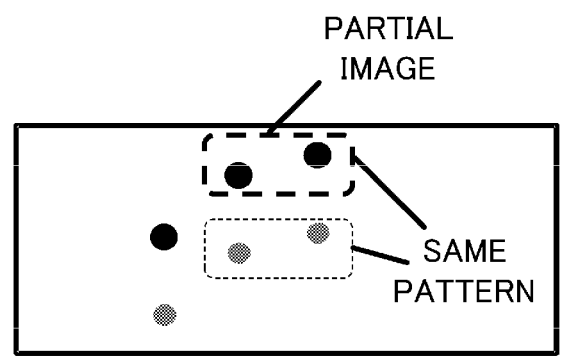

The characteristics of an artifact will now be described. If it is assumed that both surfaces of the object holding plate are substantially parallel, the multiple-reflected acoustic wave propagates back and forth over the same distance many times, and repeatedly enters the acoustic wave probe at a fixed time difference. If the acquired acoustic wave is imaged, the time delay directly appears as a spatial distance, therefore an artifact appears in a position that is separated from the light absorber image by a specific distance (FIG. 1C). This means that if the images generated by an acoustic wave reflected for a same number of times are included in one group, the spatial arrangement and the intensity relationship of the images are similar in each group (FIG. 1D).

The photoacoustic measurement apparatus according to this embodiment extracts a part of the generated whole image as a partial image, and calculates the similarities between the partial image and the whole image throughout all the areas of the whole image. As a result, it is more likely that an artifact is included in an area where the similarities are high, hence by using this approach, the operator is notified of the position of an artifact. Concrete methods of extracting a partial image and calculating the similarities between the images will be described later.

<System Configuration>

Figure 2:
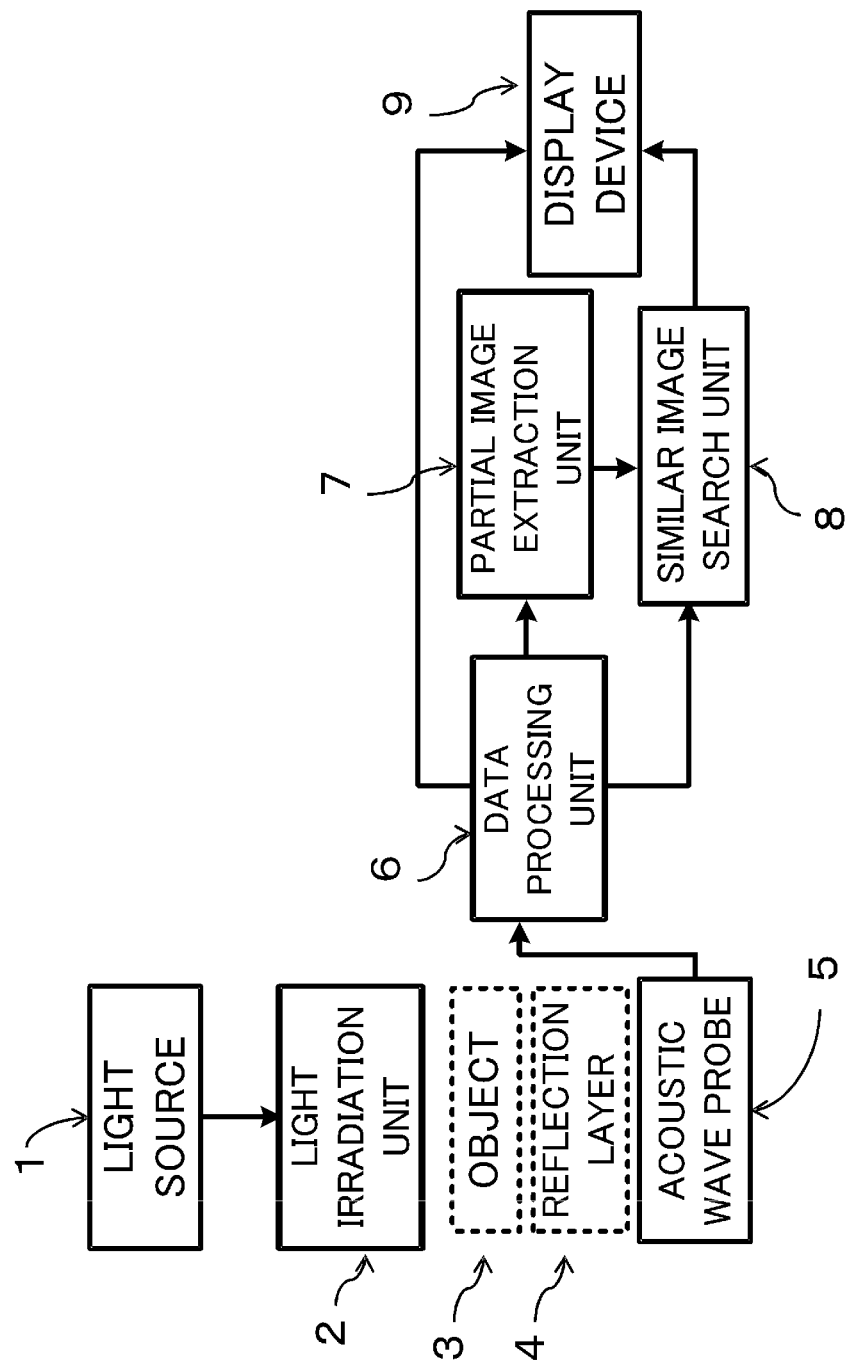
FIG. 2 is a block diagram depicting a photoacoustic measurement apparatus according to Embodiment 1.

The configuration of the photoacoustic measurement apparatus according to this embodiment will be described with reference to FIG. 2.

The photoacoustic measurement apparatus according to Embodiment 1 includes a light source 1, a light irradiation unit 2, an acoustic wave probe 5, a data processing unit 6, a partial image extraction unit 7, a similar image search unit 8 and a display device 9. In FIG. 2, the reference numeral 3 indicates an object, and the reference numeral 4 indicates a reflection layer, although neither are a part of the apparatus.

Each unit constituting the photoacoustic measurement apparatus according to this embodiment will now be described.

<<Light Source 1>>

The light source 1 generates pulsed light which is irradiated onto an object. The light source is preferably a laser light source because a laser has high power, but a light emitting diode, a flash lamp or the like may be used instead of a laser. If a laser is used for the light source, various lasers including a solid-state laser, a gas laser, a dye laser and a semiconductor laser can be used. Irradiation timing, waveform, intensity or the like are controlled by a light source control unit (not illustrated). The light source control unit may be integrated with the light source.

To effectively generate a photoacoustic wave, light must be irradiated for a sufficiently short period of time in accordance with the thermal characteristics of the object. If the object is an organism, the pulse width of the pulsed light, generated from the light source, is preferably about 10 to 50 nanoseconds. The wavelength of the pulsed light is preferably a wavelength which allows the light to propagate inside the object. In concrete terms, a wavelength of 700 nm or more, 1200 nm or less, is preferable if the object is an organism.

<<Light Irradiation Unit 2>>

The light irradiation unit 2 guides the pulsed light generated in the light source 1 to the object 3. In concrete terms, the light irradiation unit 2 is constituted by optical apparatuses including optical fiber, a lens, a mirror and a diffusion plate in order to acquire a desired beam shape and light intensity distribution. Using these optical apparatuses, the irradiation conditions of the pulsed light, such as irradiation shape of the pulsed light, light density and irradiation direction to the object can be freely set.

In order to acquire data from a wide range, the irradiation positions of the pulsed light may be changed by scanning the object with the light irradiation unit. In this case, the light irradiation unit 2 may be moved inter-locking with the acoustic wave probe, which is described later. The optical apparatuses are not limited to those of this example, but can be any apparatus that can implement the same functions.

<<Object 3>>

The object 3 and the reflection layer 4 are not composing elements of the present invention, but will be described hereinbelow. The object 3 is a target of the photoacoustic measurement, and typically is an organism. Here it is assumed that the object is a human breast, but may be a phantom simulating the characteristics of an organism.

In the photoacoustic measurement apparatus according to this embodiment, a light absorber, which exists inside the object 3 and has a large light absorption coefficient, can be imaged. If the object is an organism, the light absorber is, for example, water, lipids, melanin, collagen, protein, oxyhemoglobin or deoxyhemoglobin. If the object is a phantom, a substance simulating the optical characteristics of these substances is sealed inside the phantom as the light absorber. By imaging a light absorber inside an organism, the photoacoustic measurement apparatus according to this embodiment can perform angiography, diagnosis of malignant tumors and vascular diseases of humans and animals, and follow up observation of chemotherapy.

<<Reflection Layer 4>>

The reflection layer 4 exists between the object 3 and the acoustic wave probe 5, and is the object holding plate for holding the object 3 in this embodiment. The object holding plate is made from resin material, such as polymethylpentene or acrylic. To match the acoustic impedance, an acoustic matching material, such as acoustic matching gel, water or oil, may be interposed.

In order to suppress the reflection of an acoustic wave, it is desirable that the acoustic impedance of the object and that of the acoustic wave probe match. However the acoustic impedance cannot be perfectly matched as long as a substance, including the object holding plate, air and water, exists between the object and the acoustic wave probe, and multiple reflection is generated to some extent due to the reflection layer.

If the acoustic wave reflection surface in the reflection layer is substantially parallel with the reflection layer, the distance between the light absorber image and the artifact becomes similar in all the areas. In this case, the image can be easily searched, which means that it is desirable that the acoustic wave reflection surface of the reflection layer is substantially parallel with the reflection layer. If the acoustic wave propagation speed in the reflection layer is different from that in the object, refraction is generated on the interface therebetween, therefore it is desirable that the acoustic wave propagation speed in the reflection layer is close to the acoustic wave propagation speed of the object.

<<Acoustic Wave Probe 5>>

The acoustic wave probe 5 converts an acoustic wave generated inside the object 3 into an analog electric signal. The acoustic wave in the present invention is typically an ultrasound wave, including elastic waves called a sound waves, ultrasound waves, photoacoustic waves and light-induced ultrasound waves. The acoustic wave probe 5 may be a standalone acoustic wave probe or may be a plurality of acoustic wave probes.

The acoustic wave probe 5 may be a plurality of reception elements which are arrayed one dimensionally or two dimensionally. If multi-dimensional array elements are used, the measurement time can be decreased since the acoustic wave can be received at a plurality of locations simultaneously. If the probe is smaller than the object, the probe may scan the object so that the acoustic wave can be received at a plurality of locations.

It is preferable that the acoustic wave probe 5 has high sensitivity and a wide frequency band. In concrete terms, piezoelectric ceramics (PZT), polyvinylidene fluoride (PVDF), capacitive micro-machine ultrasonic transducer (CMUT), a Fabry-Perot interferometer or the like can be used. The acoustic wave probe 5 is not limited to the examples mentioned here, but can be any component as long as the functions of the probe can be satisfied.

<<Data Processing Unit 6>>

The data processing unit 6 generates an image by amplifying an electric signal acquired by the acoustic wave probe 5, converting it into a digital signal, and processing the digital signal. An image to indicate the distribution of an initial sound pressure due to the light absorber inside the object and an image to indicate the distribution of the absorption coefficient are generated by the data processing unit 6.

There are two types of images that are acquired by image processing. One is a reconstructed image generated by solving an inverse problem and imaging the generation source of the acoustic wave. The other type is a signal image generated by arranging the received signals according to the detected position. In Embodiment 1, an example of detecting an artifact using the reconstructed image will be described. The reconstructed image may be either two dimensional image data or three dimensional image data.

The data processing unit 6 may be a computer constituted by a CPU, a main storage device and an auxiliary storage device, or may be custom designed hardware. To acquire data efficiently, it is desirable to have a number of analog-digital converters (ADC) that is the same as the number of reception elements of the acoustic wave probe, but one ADC may be used by sequentially switching the connection.

The image reconstruction method is preferably a universal back projection method that superimposes differentiated signals, but any method may be used if an image can be reconstructed. The reconstructed image indicates an initial sound pressure distribution, which is a sound pressure of an acoustic wave generated inside the object. The initial sound pressure distribution is data which includes the attenuation information of the acoustic wave due to reflection.

In the photoacoustic diagnostic apparatus, the sound pressure decreases as the light attenuates, therefore the intensity of the signal generated inside the object becomes weaker as the location becomes deeper. Hence the initial sound pressure distribution may be divided by the light intensity distribution. Thereby an absorption coefficient distribution, which indicates the absorption coefficient of the light absorber, can be acquired.

The light intensity distribution may be calculated by measuring the irradiation distribution onto the object and calculating the propagation of the light inside the object, or may be calculated by measuring the irradiation distribution onto the object and the distribution of the light emitted from the object, and calculating the relationship therebetween. The irradiation distribution onto the object is the same unless the irradiation conditions change, therefore the irradiation distribution which is measured and stored in advance may be used. The data processing unit 6 corresponds to the whole image generation unit of the present invention.

<<Other Composing Elements>>

Other composing elements will be described here. The partial image extraction unit 7 extracts a part of the whole image acquired by the data processing unit 6 and generates a partial image, and corresponds to the partial image generation unit of the present invention. The partial image may be two dimensional image data or may be three dimensional image data. The similar image search unit 8 searches an area similar to the partial image in the whole image. A method of extracting a partial image and a method of searching an area similar to the partial image will be described later. The partial image extraction unit 7 and the similar image search unit 8 may be a computer or may be custom designed hardware, just like the case of the data processing unit 6.

The display device 9 displays the search result acquired by the similar image search unit 8 on the screen. For example, a graphic to indicate a location of an image similar to a partial image, that is a location of an artifact, is superposed and displayed on the whole image. Prior to displaying, the image may be processed, for example, by changing the transparency and the display intensity. In concrete terms, the display device 9 is a monitor having an input device, or is a touch panel display. The display device 9 may be a part of a computer.

<Method of Extracting Partial Image>

Now a method of extracting a partial image from the whole image will be described. It is necessary to extract a partial image such that one or more image(s) is/are included. The shape of an image in the partial image is preferably complex, since the accuracy of searching improves more so as the shape of the image or the positional relationship and intensity relationship of the images become more complex.

It is preferable that images included in a partial image are generated by signals which are reflected a same number of times, but even if a partial image includes signals which are reflected a different number of times, a certain level of effect can be obtained since an artifact generated by further reflection can be searched. If the whole image is three dimensional volume data, it is preferable that the partial image is also three dimensional volume data. The partial image is preferably extracted automatically, but may be extracted manually.

Two types of methods of automatically extracting a partial image will be described.

(1) Method Using Brightness

A first method is a method of extracting a partial image using the brightness (pixel values) of pixels.

In a case of measuring an organism by the photoacoustic measurement apparatus, a signal having the highest intensity is a signal corresponding to a blood vessel located near the surface of an object. An artifact, on the other hand, is a signal generated by an acoustic wave which entered the acoustic wave probe after propagating through the reflection layer, so the intensity thereof is relatively low. Therefore if an area of which brightness is high (that is, signal intensity is high) is selected, an image of a signal which did not reflect at all can be acquired. In concrete terms, a predetermined threshold is set for the brightness of the pixels of the whole image, then a rectangular area enclosed by the maximum coordinates and the minimum coordinates of an image constituted by the pixels of which brightness is the threshold or higher is determined as an area of the partial image, and is extracted from the whole image.

Figure 3A:
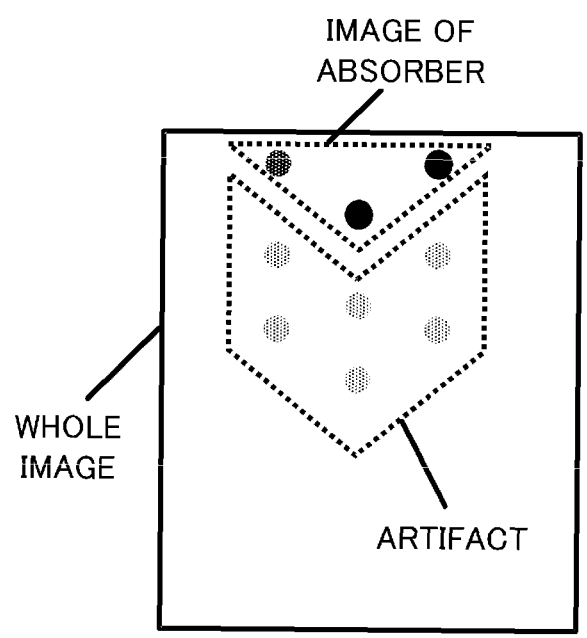
FIG. 3A to FIG. 3D are diagrams depicting a method of extracting a partial image.
Figure 3B:
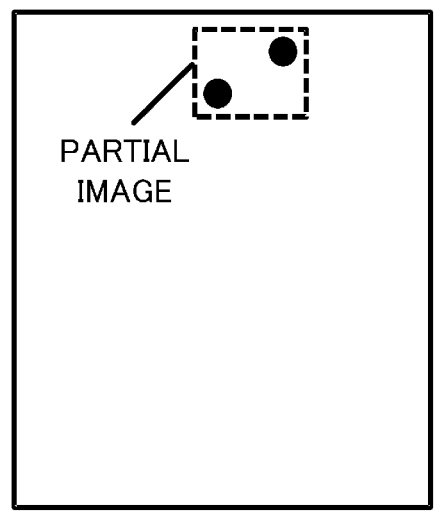

FIG. 3A is a diagram depicting the acquired whole image, and the upper side is the acoustic wave probe side. Therefore the artifact generated by the reflection appears in a position more distant from the image of the absorber when viewed from the acoustic wave probe. In the drawing, it is assumed that the darker color indicates higher brightness. By this method, the partial image is extracted as illustrated in FIG. 3B.

It is preferable that after extracting the partial image, image processing to enhance the image of the absorber is performed on the whole image. Thereby the extraction accuracy can be improved, and as a result the search accuracy can be improved. In concrete terms, filter processing, such as smoothing and sharpening, and characteristic pattern extraction of the absorber image, for example, can be performed. Out of the voxels that reach or exceed the threshold, a small cluster of voxels may be removed using such image processing as morphology since this cluster is very likely due to noise, so that a rectangular area enclosed by the maximum coordinates and the minimum coordinates of the image is extracted as a partial image from the whole image.

An area with some additional margin to the maximum coordinates and to the minimum coordinates of the voxels that reach or exceed the threshold may be regarded as a partial image. The processing using the threshold may be performed based on classification processing, such as discriminant analysis and support vector machine algorithms. By combining the above described processes, the accuracy of extracting a partial image can be improved, and the search accuracy can be improved.

(2) Method of Using Position

The second method is a method of extracting a partial image based on position.

In this method, an area enclosed by a surface of an object and surfaces located at a predetermined distance from the surface of an object is extracted as a partial image from the whole image. Delays in multiple reflection signals are determined by the thickness of the reflection layer and the propagation speed of an acoustic wave inside the reflection layer. Therefore if the thickness of the reflection layer and the propagation speed of the acoustic wave are known, the delay time can be determined, whereby a location in the whole image where the first reflection signal appears can be calculated. All signals in an area closer to the acoustic wave probe from the first reflection signal form an image of the absorber without reflection, hence a partial image can be extracted from this area. All areas of this area are regarded as a partial image in this embodiment.

Figure 3C:
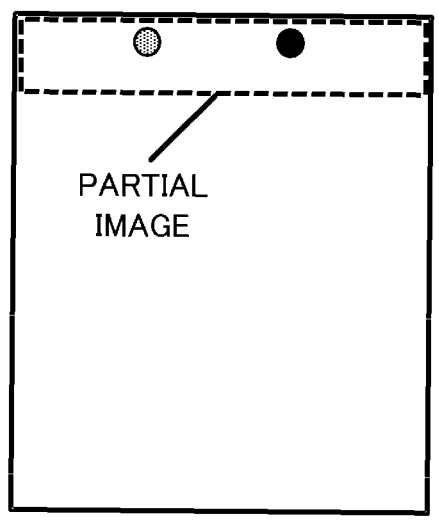

According to this method, a partial image is extracted as shown in FIG. 3C. The distance from the surface of the object, to extract the partial image, may be changed adaptively based on the acquired information on the thickness of the reflection layer and the acoustic wave propagation speed. Thereby even if the thickness of the reflection layer and the acoustic wave propagation speed change depending on the measurement, a partial image can be extracted. The surface of the object and the surfaces located at a predetermined distance may be curved surfaces. This means that a partial image can be accurately extracted even if it is difficult to flatten the object, such as the case when the object is an organism. If the second method is used, even an absorber image of which brightness is low can be included in the extracted partial image.

Figure 3D:
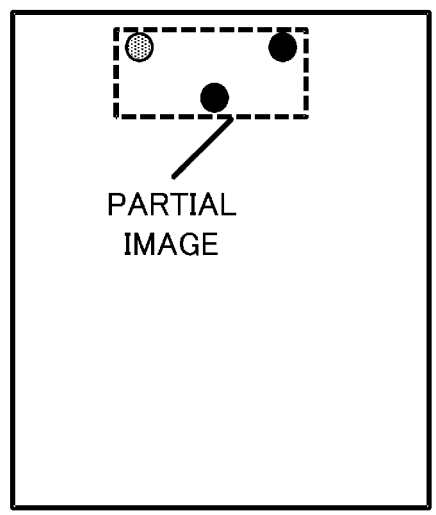

A partial image may be extracted by a combination of the first method and the second method. Then only the absorption image can be accurately extracted as shown in FIG. 3D.

<Search Method>

Now a method of searching an area that matches with a partial image, out of the whole image, will be described. In the search processing, a location of an image having a similar shape as the partial image is searched in the whole image.

Figure 4A:
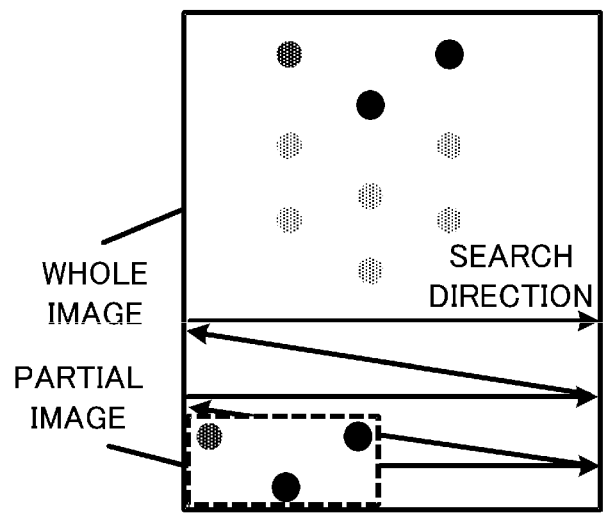
FIG. 4A to FIG. 4C are diagrams depicting a matching method between a whole image and a partial image.

There are many methods to implement this search, but in this embodiment, template matching using the partial image as a template image is performed. As illustrated in FIG. 4A, according to the template matching, cross-correlation of the partial image and the whole image is calculated while changing the location of the partial image, and correlation, that is the similarities, of these images are determined.

In the case of calculating the similarities by scanning and using the partial image like this, each of the calculated similarity values is plotted on the reference point of the partial image (hereafter called "partial image reference point") on the respective location, and a distribution of similarities is acquired. The partial image reference point may be an origin of the partial image or may be a point where the brightness is highest in the partial image. Normally an artifact has lower brightness, therefore it is desirable to calculate using zero-mean normalized cross-correlation (ZNCC) by matching the offset of the brightness, as indicated by Mathematical Expression 1. Alternatively such a calculation using normalized cross-correlation (NCC) indicated by Mathematical Expression 2 or sum of squared difference (SSD) indicated by Mathematical Expression 3 may be used. Furthermore, sum of absolute difference (SAD) indicated by Mathematical Expression 4 may be used instead.

[Math 1]

$$R(I_1, I_2) = \frac{\sum (I_1 - I_{avg1})(I_2 - I_{avg2})}{\sqrt{\sum (I_1 - I_{avg1})^2 \times \sum (I_2 - I_{avg2})^2}} \quad (1)$$

[Math. 2]

$$R(I_1, I_2) = \frac{\sum I_1 I_2}{\sqrt{\sum I_1^2 \times \sum I_2^2}} \quad (2)$$

[Math. 3]

$$R(I_1, I_2) = \sum (I_1 - I_2)^2 \quad (3)$$

[Math. 4]

$$R(I_1, I_2) = \sum |I_1 - I_2| \quad (4)$$

Figure 4B:
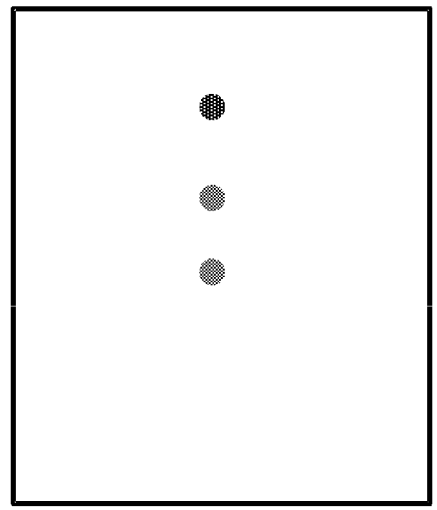

Here $R(I_1, I_2)$ is a similarity of the vectorized images $I_1$ and $I_2$. $I_{avg1}$ is an average brightness value if $I_1$ and $I_{avg2}$ is an average brightness value of $I_2$. For the search processing, a convolution operation of the partial image and the whole image may be performed after matching the size of the partial image with the whole image by zero padding, or cross-correlation may be calculated after converting the whole image and the partial image into phase images (by a phase restriction correlation method). Alternatively, other methods used for pattern recognition in image processing may be used. By performing search processing, the distribution indicating similarities of the partial image and the whole image are acquired as illustrated in FIG. 4B.

<Measurement Processing Flow Chart>

Figure 5:
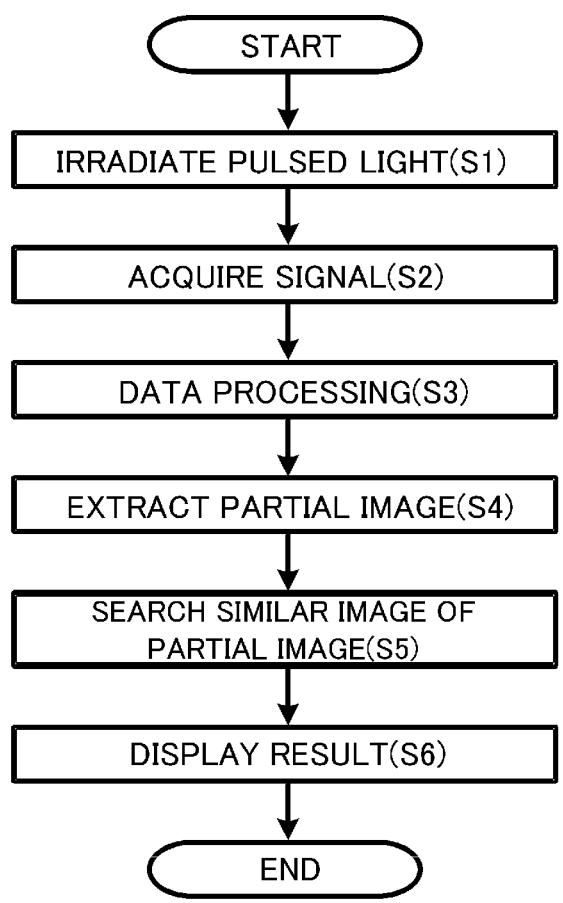
FIG. 5 is a flow chart depicting processing of the photoacoustic measurement apparatus according to Embodiment 1.

FIG. 5 is a flow chart depicting the processing by the photoacoustic measurement apparatus according to this embodiment. First pulsed light is irradiated from the light source 1 onto an object through the light irradiation unit 2 (S1), then photoacoustic wave generated inside the object is received by the acoustic wave probe 5, and the data processing unit 6 acquires the signal data (S2). Then data processing, including reconstruction processing, is performed using the acquired signal data, whereby the whole image is generated (S3).

Then the partial image extraction unit 7 extracts a partial image from the acquired whole image using the method described above (S4). Then the similar image search unit 8 searches an area similar to the partial image in the whole image using the method described above (S5). The search may be performed by specifying all the areas of which a similarity R is the threshold or more. Thereby a rectangular area where an artifact is estimated to exist can be specified.

Figure 4C:
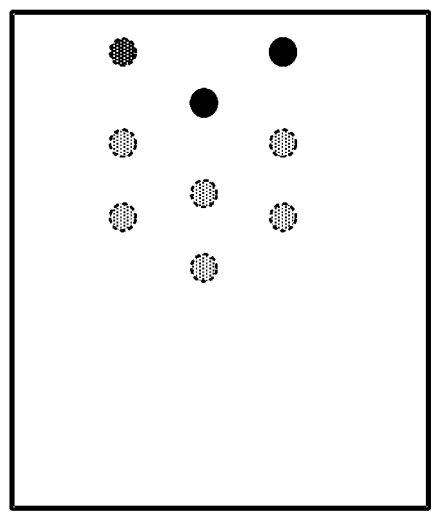

Finally the display device 9 displays the search result (S6). For the display method, it is preferable to superimpose an indicator on the whole image to indicate an artifact, as illustrated in FIG. 4C. Thereby the position of the artifact can be highlighted and notified to the operator such that the operator can recognize the artifact intuitively. In the example of FIG. 4C, the dotted line encircling the image is the indicator. The indicator can be displayed by extracting the contour from the partial image in advance, differentiating the distribution of similarities between the partial image and the whole image acquired by the search processing to determine the coordinates of the maximum value, matching the partial image reference points with the coordinates in the whole image, and superposing the contour of the image there.

The indicator may be displayed by a method other than the method of enclosing the area with a dotted line or line. For example, an arrow mark may be superposed on the display, or a partial image of which color is different from the whole image may be superposed on the display. Instead of determining the maximum value, the coordinates may be identified by trying to "fit" a similarity distribution model acquired by calculation or experiment.

Furthermore, a threshold may be set for the similarity distribution, so that the extracted contour of a partial image may be superposed and displayed for all the coordinates that reach or exceed the threshold. Display and non-display of an indicator may be switchable.

The indicator need not always be displayed on the whole image in the superposed state. For example, an image to indicate the similarity distribution may be displayed independently, or only the coordinates may be displayed. Any display method can be used if it can be indicated where the image similar to the partial image is located in the whole image.

Thus the photoacoustic measurement apparatus according to Embodiment 1 can notify the operator of a location of an artifact generated by the multiple reflection, whereby the accuracy of the photoacoustic measurement can be improved.

In Embodiment 1, it is assumed that the interface of the object holding plate is substantially parallel with the other surface of the object holding plate, but if not, a location where an artifact appears shifts. To handle this problem, such a processing as transforming the partial image in accordance with the shape of the object holding plate may be performed, so that the processed partial image can be used for searching.

Embodiment 2

In Embodiment 1, the whole image and the indicator are superposed on the display, whereby the operator is notified of the presence of an artifact. In Embodiment 2, on the other hand, an artifact is automatically removed from the whole image.

Figure 6:
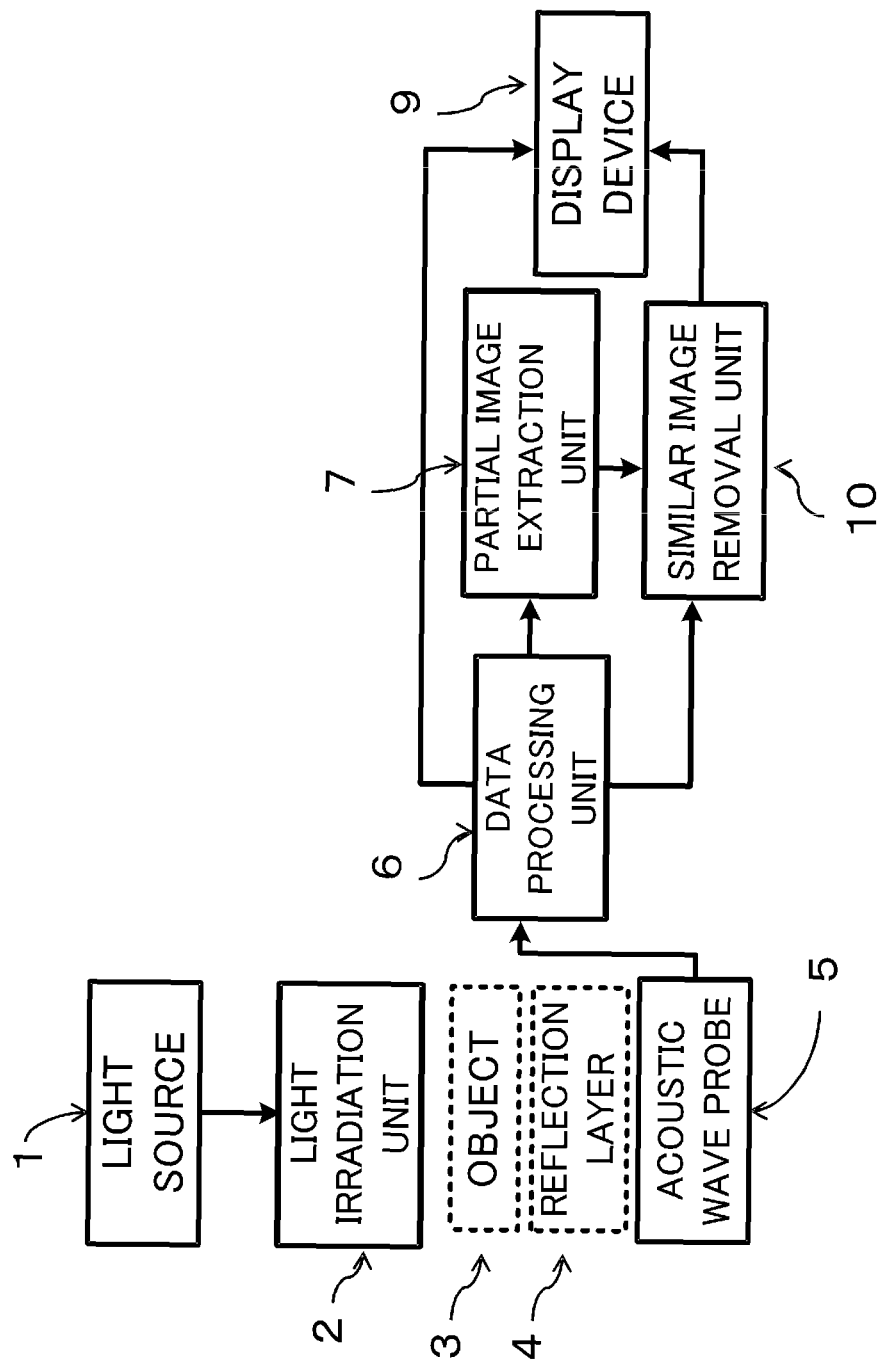
FIG. 6 is a block diagram depicting a photoacoustic measurement apparatus according to Embodiment 2.

FIG. 6 shows a configuration of a photoacoustic measurement apparatus according to Embodiment 2. In Embodiment 2, the similar image removal unit 10 is included instead of the similar image search unit 8. A same composing element as Embodiment 1 is denoted with a same reference number, for which description is omitted.

The similar image removal unit 10 removes any image similar to a partial image from the whole image, and generates an image where an artifact, due to multiple reflection, has been removed.

The artifact removal operation performed by the similar image removal unit 10 according to Embodiment 2 will be described with reference to the processing flow chart in FIG. 7.

The whole image is an image combining an image generated by the signals which did not reflect, an artifact and the other images. In other words, the image generated by the signals which did not reflect and the artifact can be regarded as a partial image, which is superposed on the whole image. Therefore if such an objective function J in Mathematical Expression 5 is defined and an optimization operation to minimize J is performed, an image generated by the signals which did not reflect and an image X which indicates the distribution of the artifact can be acquired (step S7). Here B is the whole image and A is the partial image. X is an image which becomes a variable to indicate the coordinates of which the partial image is superposed and the intensity when the partial image is superposed.

[Math. 5]

$$J = \Sigma |B - AX| \quad (5)$$

Then as Mathematical Expression 6 shows, the extracted image is deleted from the whole image, whereby an image $I_r$, where the image generated by the signal which did not reflect and the artifact are removed, is acquired (step S8). Here $X_{J \to min}$ denotes X to minimize the objective function J.

[Math. 6]

$$I_r = B - A \, X_{J \to min} \quad (6)$$

The image acquired by Mathematical Expression 6 is an image where the image, generated by the signals which did not reflect, is also removed, hence in the final step, a processing to paste the partial image extracted by the partial image extraction unit 7 onto the original coordinates is performed. Thereby an image where only the artifact is removed can be acquired (step S9).

Figure 7:
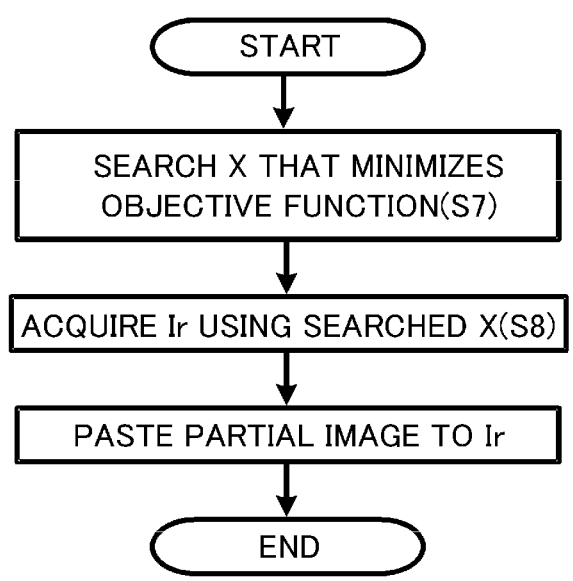
FIG. 7 is a flow chart depicting processing of the photoacoustic measurement apparatus according to Embodiment 2.

The processing flow in Embodiment 2 is the same as that in Embodiment 1, except that the processing in step S5 in Embodiment 1 is replaced with the processing in step S7 to S9 shown in FIG. 7. Another difference is that the image displayed in step S6 is the image generated by the similar image removal unit 10.

The photoacoustic measurement apparatus according to Embodiment 2 can provide a measurement image to the operator after an artifact, due to multiple reflection, is removed.

When the image after the artifact is removed is provided to the operator, the image before the artifact is removed may also be displayed side by side on the display. Thereby the operator can confirm the result of artifact removal.

Embodiment 3

Embodiment 3 is an embodiment to remove an artifact as in Embodiment 2, but an artifact is not removed from the reconstructed image, instead multiple reflection signals are removed from a signal image and the image is reconstructed after the removal, whereby an image free of artifacts can be acquired.

Figure 9A:
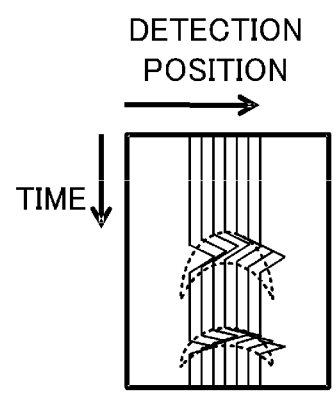
FIG. 9A and FIG. 9B are diagrams depicting how to remove a multiple reflection signal from a signal image.

The signal image is an image to indicate the intensity of the received acoustic wave signal, where the amplitude of the acoustic wave signal is indicated by color shading. As illustrated in FIG. 9A, a signal image is generated by plotting the intensity of the acoustic wave signal which an acoustic wave probe received on each detected position. The signal image is an image represented by time and position, hence the multiple reflection signals can be removed using the same method as Embodiment 2. If multiple reflection signals are removed from the signal image and the image is then reconstructed, a reconstructed image, where an artifact has been removed, can be acquired.

Figure 8:
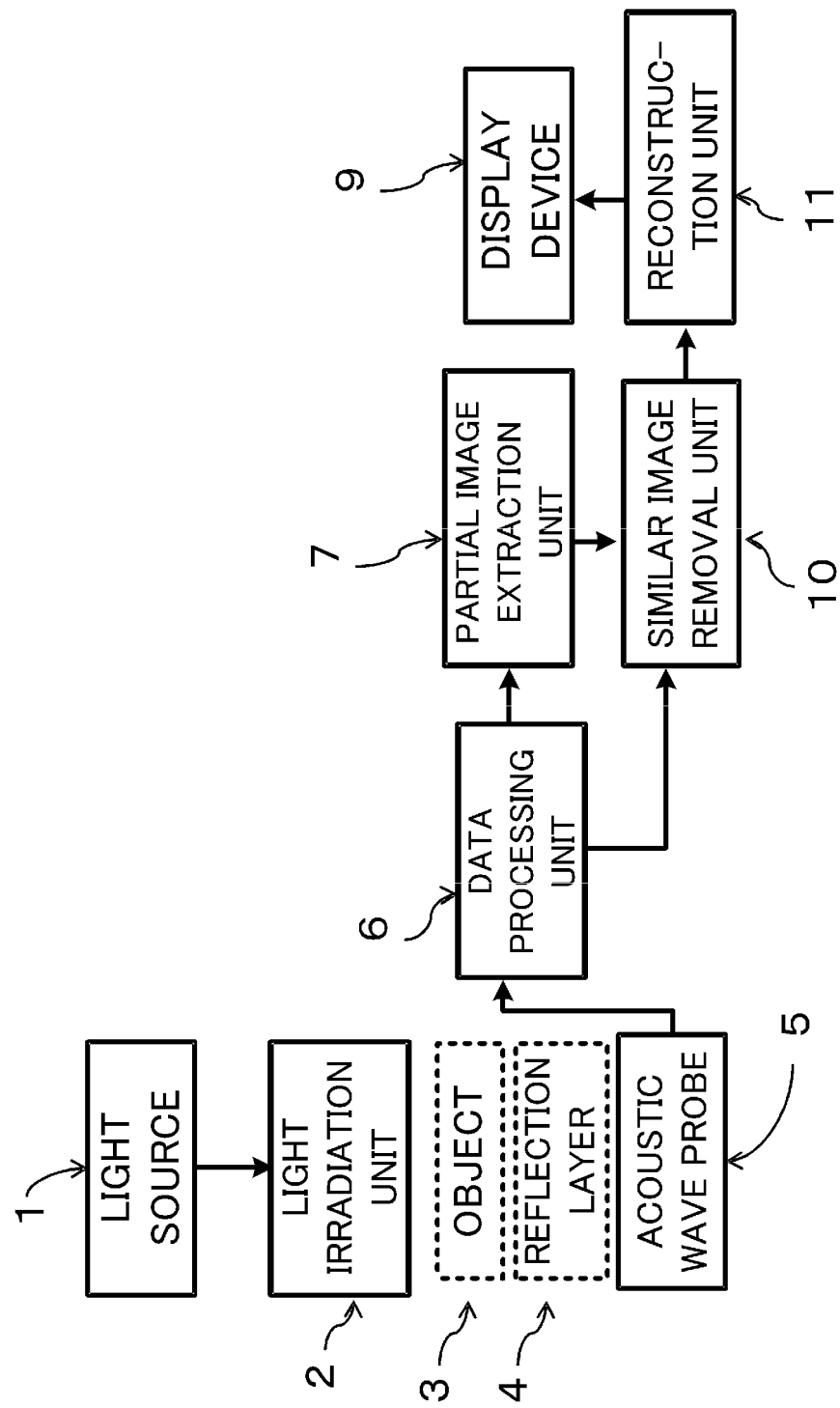
FIG. 8 is a block diagram depicting a photoacoustic measurement apparatus according to Embodiment 3.

FIG. 8 shows a configuration of a photoacoustic measurement apparatus according to Embodiment 3. Differences of the photoacoustic measurement apparatus according to Embodiment 3 from Embodiment 2 are that a reconstruction unit 11, to reconstruct an image, is included, and that the data processing unit 6 performs different processing. These differences will now be described.

Figure 9B:
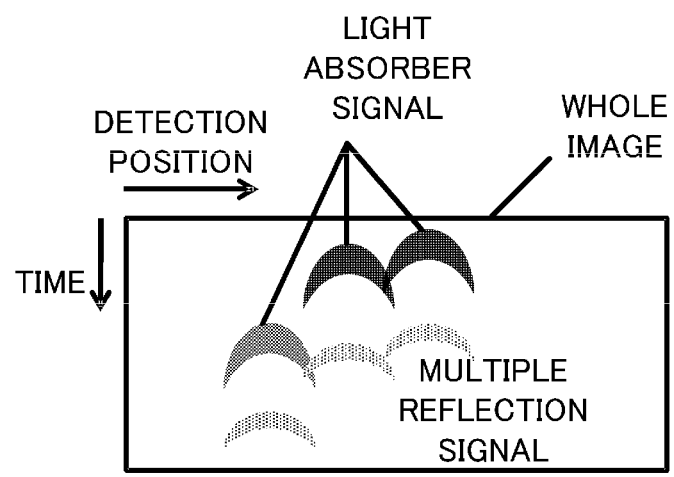

The data processing unit 6 according to Embodiment 3 generates a signal image by arranging the signals acquired at different positions corresponding to the detected positions, as described above (FIG. 9A). The signal image of the measurement system illustrated in FIG. 1A becomes as shown in FIG. 9B. Here the wave height (amplitude) of a signal is indicated by color shading. Even in the signal image, signals that appear due to multiple reflection exhibit a spatial arrangement and an intensity relationship similar to those of the artifacts that appear on the reconstructed image. Therefore the multiple reflection signals can be removed by a method the same as Embodiment 2.

The reconstruction unit 11 performs image reconstruction processing based on the signal image where multiple reflection signals have been removed, and reconstructs the image. The content of the reconstruction processing is the same as Embodiment 2.

In Embodiment 3, as described above, the multiple reflection signals are removed using the signal image before reconstructing the image, hence a natural image can be acquired even in a case when an artifact cannot be removed well from the reconstructed image.

In this embodiment, the multiple reflection signals are removed using the signal image, but only processing to discern the multiple reflection signal may be performed, as in the case of Embodiment 1, and an indicator to indicate a position of an artifact in the reconstructed image may be generated.

Embodiment 4

As illustrated in FIG. 4A, in Embodiment 1 to Embodiment 3, the partial image is matched with the whole image and similarity is calculated, while changing the location of the partial image. However an artifact appears only in a direction where the acoustic wave is reflected, and performing matching processing in other areas is not only unnecessary but also may cause detection errors. Embodiment 4 is an embodiment to improve the determination accuracy by limiting the search direction of the partial image.

The only difference of the photoacoustic measurement apparatus according to Embodiment 4 from Embodiment 1 is the processing performed by the similar image search unit 8.

The similar image search unit 8 according to Embodiment 4 stores a shape of the reflection layer and a direction where an artifact appears on an image in advance. The direction where an artifact appears is preferably calculated by simulating the propagation of the acoustic wave, but may be calculated analytically or geometrically.

Figure 10:
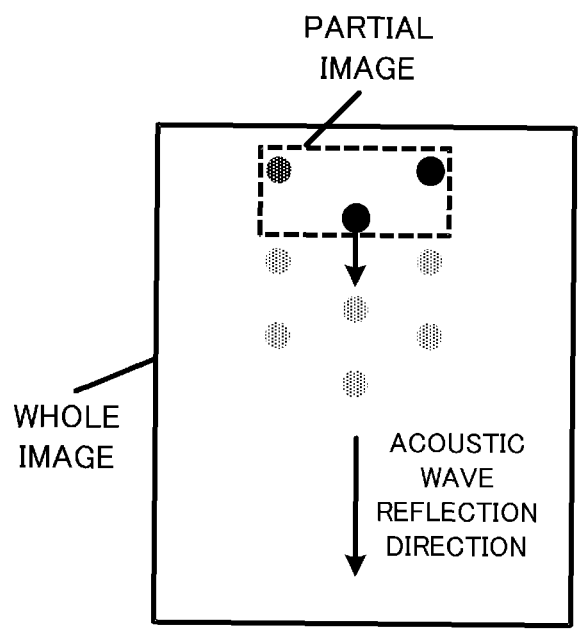
FIG. 10 is a diagram depicting a method of searching a partial image according to Embodiment 4.

According to Embodiment 4, when the processing in step S5 is executed, similarity is calculated while moving the partial image which is extracted from the whole image, from the extracted position in the direction where the acoustic wave is reflected, as illustrated in FIG. 10. In the example in FIG. 10, the direction where the acoustic wave is reflected is the direction from a surface layer to a deeper layer, that is, from the top to the bottom in the drawing.

In Embodiment 4, matching processing is not performed in an area where an artifact does not appear, hence the time required searching for an artifact can be reduced. Furthermore, detection errors can be decreased, and detection accuracy can be improved.

EXAMPLES

Effects of the present invention was confirmed by experiments. In this example, the object is a breast of an organism held between two 10 mm thick polymethylpentene plates, which closely contact both sides of the object, a 1 mm thick oil layer is applied to the opposite side of one of the holding plates, and the acoustic wave probe is contacted via this oil layer. Caster oil is used for the oil layer, and the acoustic wave probe is constituted by 15×23 PZT elements which are arrayed in the plane direction, where the reception unit of each element has a 2 mm diameter, and an 80% band with a 1 MHz central frequency.

The acoustic probe is connected to an X-Y stage so that scanning in the same plane direction as the plane of the acoustic wave probe is possible. The light irradiated onto the object is a nanosecond order of pulsed light (wavelength: 797 nm) using a TiS laser. This pulsed light is irradiated from the same surface as the acoustic probe and the opposite surface, which is across from the object, at the same time, collection of the acoustic wave signals and scanning are repeated, and complete signal data is acquired. The A/D convertor that is used has a 20 MHz sampling frequency and a 12-bit resolution, and a reconstructed image is acquired using back projection.

FIG. 11 is a part of the acquired reconstructed images. The reconstructed images are three dimensional image data, but for description here, a two dimensional image (a sliced image) generated by slicing the three dimensional image data on an X-Y plane is used. A voxel is the unit of scale in FIG. 11.

Figure 11A:
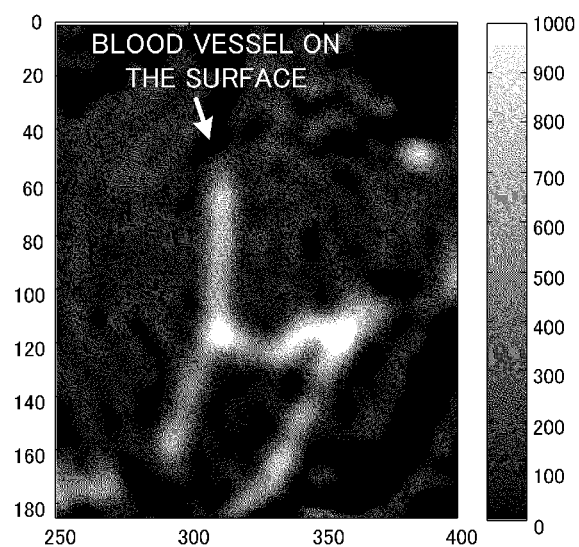
FIG. 11A to FIG. 11F are images acquired by examples corresponding to each embodiment.
Figure 11B:
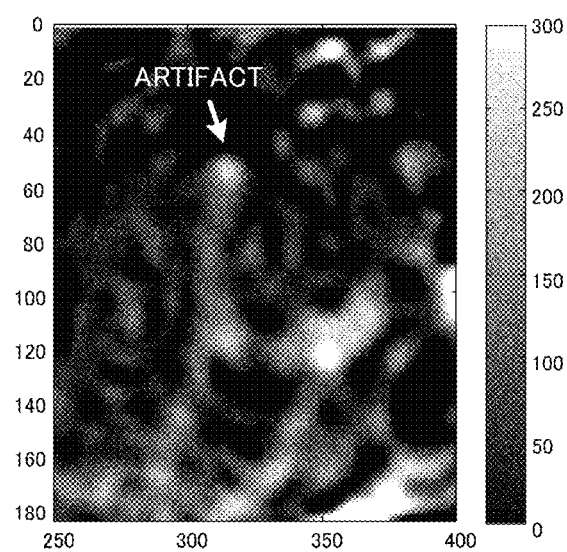
Figure 11C:
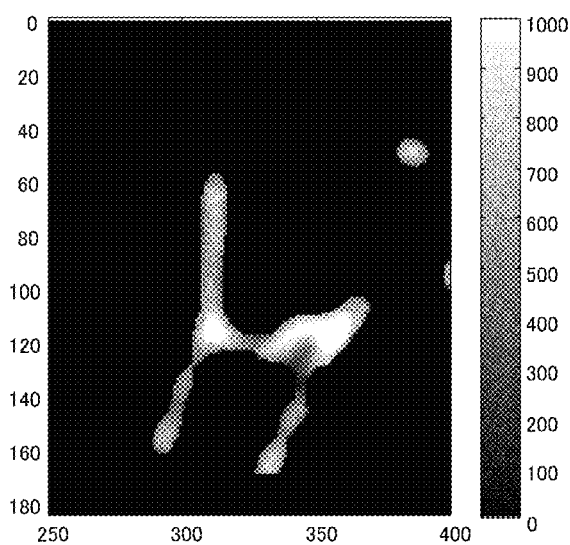

FIG. 11A is an image generated by slicing the reconstructed image at a depth where an image of surface blood vessels can be observed, and FIG. 11B is an image generated by slicing the reconstructed image at a position that is deeper than FIG. 11A. This shows that artifacts generated by the respective image of the surface blood vessels in FIG. 11A and FIG. 11B appear as very similar shapes. FIG. 11C is an image generated by slicing an extracted partial image. The partial image is extracted by performing processing to enhance the image first, then using the position of the image and the signal intensity (brightness).

Figure 11D:
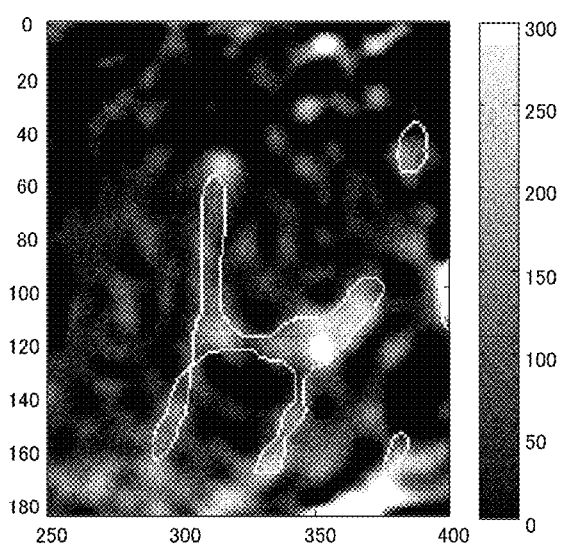

Zero-mean normalized cross-correlation (ZNCC) is used to search a partial image. FIG. 11D is an image corresponding to Embodiment 1, where the artifact that appeared in FIG. 11B is shown by the indicator (white frame). The indicator to highlight the artifact is displayed at the same location as in FIG. 11B. By displaying the indicator on the whole image like this, the artifact can easily be recognized.

Figure 11E:
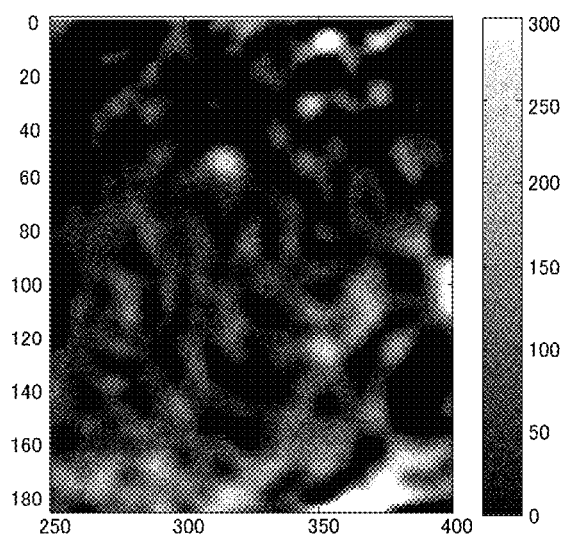

FIG. 11E is an image corresponding to Embodiment 2, and is a whole image after the artifact is removed from the image in FIG. 11B. Compared with FIG. 11B, the artifact obviously appears to be reduced.

Figure 11F:
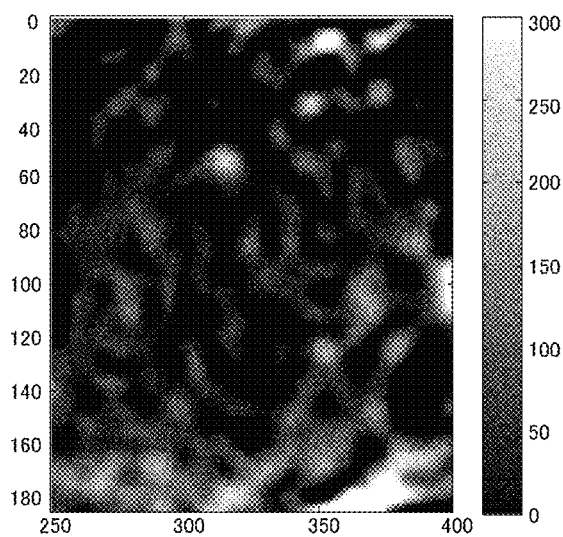

FIG. 11F is an image corresponding to Embodiment 3. In other words, FIG. 11F shows a whole image when the artifact was determined using a signal image, and removed. Compared with FIG. 11B, the artifact clearly appears to be reduced.

In the above examples, the artifact has a shape that is easy to identify, but an artifact of which shape is simple or an artifact generated after many reflections is hard to visually discern. Even in such a case, the photoacoustic measurement apparatus according to the present invention can discern an artifact by extracting an are area similar to the partial image from the whole image.

(Modification)

The description of the embodiments is merely examples used for describing the present invention, and various changes and combination thereof are possible to carry out the invention without departing from the true spirit of the invention. The present invention can also be carried out as a control method for an object information acquiring apparatus that includes at least a part of the above mentioned processing. The above mentioned processing and means can be freely combined to carry out the invention as long as there is no technical inconsistency generated.

In the respective embodiments, similarity is calculated while shifting the partial image, but it is not always necessary to calculate similarity for the whole area. For example, search is performed from a surface layer to a deeper layer, and an area where similarity is highest (that is, an artifact where the signal intensity is highest) is detected first, then a position of an artifact that appears at an even deeper layer is estimated using a distance determined by multiplying the distance between the partial image and this area.

The respective embodiments were described using a photoacoustic measurement apparatus as an example, but the present invention may be applied to an ultrasound measurement apparatus which transmits an ultrasound wave to an object and visualizes information inside the object by receiving the ultrasound wave reflected inside the object. The present invention can be applied to any apparatus that visualizes information inside the object by analyzing an acoustic wave that has arrived from inside the object.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-095196, filed on Apr. 30, 2013, which is hereby incorporated by reference herein in its entirety.

What is claimed is:

1. An object information acquiring apparatus that acquires information inside an object by receiving an acoustic wave that has arrived from inside the object through a layer having an acoustic impedance that is different from that of the object, and analyzing the acoustic wave, the object information acquiring apparatus comprising:

an acoustic wave probe that receives an acoustic wave and converts the acoustic wave into an electric signal;

a whole image generation unit that generates a whole image, which is an image indicating information inside the object, based on the electric signal after the conversion;

a partial image generation unit that extracts a partial image, which is a part of the whole image, from the whole image; and a similar image search unit that searches an area similar to the partial image, from the whole image, wherein the similar image search unit searches an area similar to the partial image from a start position, which is a position where the partial image has been extracted, in a direction where the acoustic wave that has arrived from inside the object is reflected by the layer having acoustic impedance that is different from that of the object.

2. The object information acquiring apparatus according to claim 1, wherein the similar image search unit specifies a false image that has appeared on the whole image, based on the search result.

3. The object information acquiring apparatus according to claim 2, further comprising:
a display unit that displays the whole image and highlights a false image specified by the similar image search unit.

4. The object information acquiring apparatus according to claim 2, further comprising:
a removal unit that removes a false image specified by the similar image search unit, from the whole image; and
a display unit that displays the whole image after the removing unit removes the false image.

5. The object information acquiring apparatus according to claim 1, wherein the partial image generation unit determines an area to extract a partial image, based on pixel values of pixels of the whole image.

6. The object information acquiring apparatus according to claim 5, wherein the partial image generation unit extracts, as a partial image, an area constituted by pixels having a brightness of a predetermined value or more, out of the whole image.

7. The object information acquiring apparatus according to claim 1, wherein the partial image generation unit determines an area to extract a partial image, based on the location of the area in the whole image.

8. The object information acquiring apparatus according to claim 7, wherein the partial image generation unit extracts a partial image from an area of which distance from a surface of the object is shorter than a predetermined value, out of the whole image.

9. The object information acquiring apparatus according to claim 2, wherein the whole image is an image that indicates an intensity of the received acoustic wave,
and the object information acquiring apparatus further comprising:
a reconstruction unit that reconstructs an image by performing operation on the whole image; and
a display unit that displays the reconstructed image and highlights the false image specified by the similar image search unit.

10. The object information acquiring apparatus according to claim 2, wherein the whole image is an image that indicates an intensity of the received acoustic wave,
and the object information acquiring apparatus further comprising:
a removal unit that removes the false image specified by the similar image search unit, from the whole image;
a reconstruction unit that reconstructs an image by performing operation on the whole image after the false image is removed; and
a display unit that displays the reconstructed image.

11. The object information acquiring apparatus according to claim 1, wherein
the layer having an acoustic impedance that is different from that of the object is a holding plate that holds the object, and
the acoustic wave probe receives, through the holding plate, the acoustic wave that has arrived from inside the object.

12. The object information acquiring apparatus according to claim 1, further comprising a light irradiation unit that irradiates light onto the object,
wherein the acoustic wave is a photoacoustic wave generated inside the object due to the light.

13. A control method of an object information acquiring apparatus that has an acoustic probe to receive an acoustic wave, and acquires information inside an object by receiving an acoustic wave that has arrived from inside the object through a layer having an acoustic impedance that is different from that of the object and analyzing the acoustic wave, the control method comprising:
a reception step of receiving an acoustic wave and converting the acoustic wave into an electric signal using the acoustic wave probe;
a whole image generation step of generating a whole image, which is image indicating information inside the object, based on the electric signal after the conversion;
a partial image generation step of extracting a partial image, which is a part of the whole image, from the whole image; and
a similar image search step of searching an area similar to the partial image, from the whole image,
wherein in the similar image search step, an area similar to the partial image is searched from a start position, which is a position where the partial image has been extracted, in a direction where the acoustic wave that has arrived from inside the object is reflected by the layer having an acoustic impedance that is different from that of the object.

14. The object information acquiring apparatus according to claim 1, wherein the partial image generation unit extracts the image corresponding to the blood vessel located near the surface of the object, from the whole image, as the partial image.

15. The object information acquiring apparatus according to claim 3, wherein the display unit highlights the false image using an indicator.

16. The object information acquiring apparatus according to claim 3, wherein the display unit highlights the false image using a different color from the whole image.

* * * * *